US008694086B2

(12) United States Patent
Hampton

(10) Patent No.: US 8,694,086 B2
(45) Date of Patent: Apr. 8, 2014

(54) SYSTEMS AND METHODS FOR NON-INVASIVELY RECORDING ECG IN CONSCIOUS AMBULATORY SUBJECTS

(75) Inventor: Thomas G. Hampton, Framingham, MA (US)

(73) Assignee: Mouse Specifics, Inc., Quincy, MA (US)

( * ) Notice: Subject to any disclaimer, the term of this patent is extended or adjusted under 35 U.S.C. 154(b) by 0 days.

(21) Appl. No.: 13/359,071

(22) Filed: Jan. 26, 2012

(65) Prior Publication Data

US 2012/0190995 A1     Jul. 26, 2012

Related U.S. Application Data

(60) Provisional application No. 61/462,001, filed on Jan. 26, 2011, provisional application No. 61/462,598, filed on Feb. 4, 2011.

(51) Int. Cl.
*A61B 5/0402* (2006.01)
*A61B 5/0432* (2006.01)

(52) U.S. Cl.
USPC ............ 600/523; 600/509; 600/511; 600/524

(58) Field of Classification Search
USPC ................................. 600/509, 511, 523, 524
See application file for complete search history.

(56) References Cited

U.S. PATENT DOCUMENTS

| | | | |
|---|---|---|---|
| 4,051,812 A * | 10/1977 | DeLoach et al. ............ | 119/51.11 |
| 4,247,756 A * | 1/1981 | Cucinotta et al. ............. | 219/528 |
| 6,445,941 B1 | 9/2002 | Hampton et al. | |
| 6,535,754 B2 * | 3/2003 | Fishbein et al. ............. | 600/422 |
| 6,837,184 B2 * | 1/2005 | Gondhalekar et al. ........ | 119/421 |
| 6,875,418 B2 * | 4/2005 | Hampton ....................... | 424/9.1 |
| 6,899,686 B2 * | 5/2005 | Hampton et al. ............. | 600/595 |
| 7,065,396 B2 | 6/2006 | Hampton | |
| 7,096,059 B2 * | 8/2006 | Geddes et al. ................ | 600/509 |

OTHER PUBLICATIONS

Fischmann, et al., "Clinical Trial of a Balsa-Lithium Electrode for Conventional Electrocardiography", The American Journal of Cardiology, 10(6):846-851 (1962).

* cited by examiner

*Primary Examiner* — Niketa I. Patel
*Assistant Examiner* — Christopher A Flory
(74) *Attorney, Agent, or Firm* — Morse, Barnes-Brown & Pendleton, P.C.; Sean D. Detweiler, Esq.

(57) ABSTRACT

An apparatus for non-invasively measuring an electrocardiogram (ECG) in a conscious ambulatory subject includes an electrically conductive platform. The electrically conductive platform establishes an electrical connection with the subject at one of a position forward (e.g., rostral to) or a position rearward (e.g., caudal to) the heart. An additional electrical connection is established at the other of a position forward (e.g., rostral to) or a position rearward (e.g., caudal to) on the subject. The position rearward to (e.g., caudal to) the heart can be the tail of the subject. The additional electrical connection can be established by a movable electrode, an electrically conductive ringlet, an additional electrically conductive platform, a region of conductive material, an electrically conductive dome, a food element, or one or more electrically conductive posts.

9 Claims, 16 Drawing Sheets

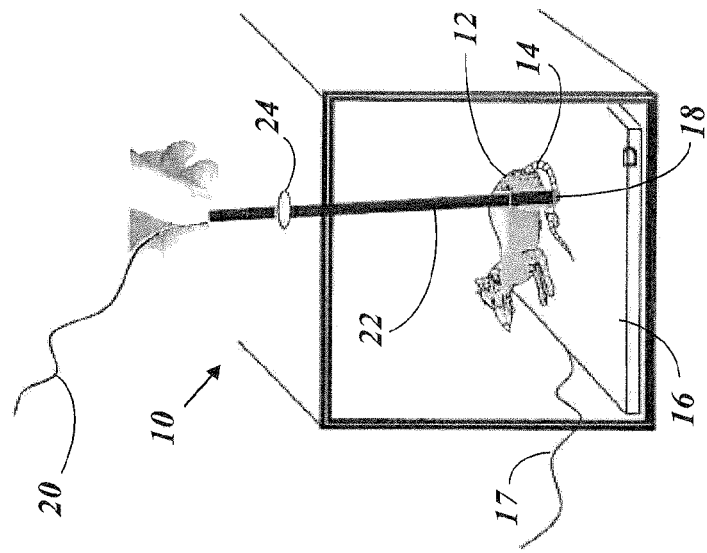
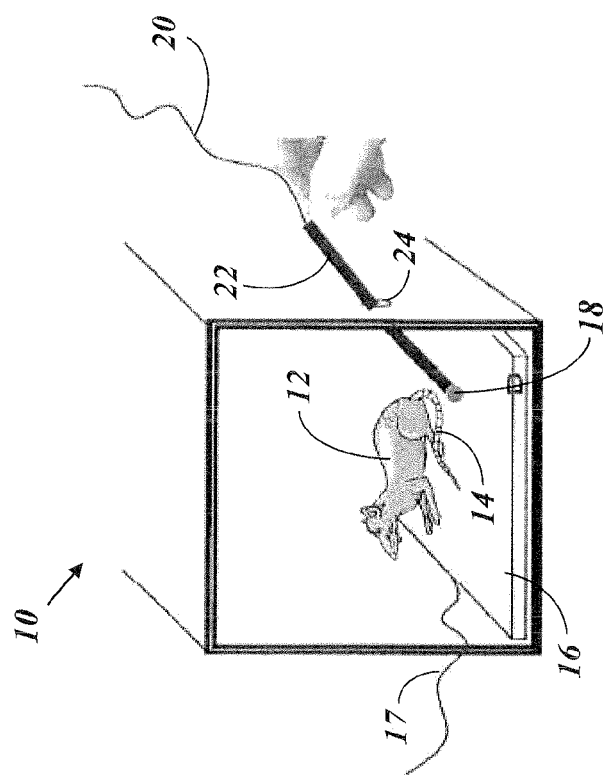
FIG. 3B
FIG. 3A

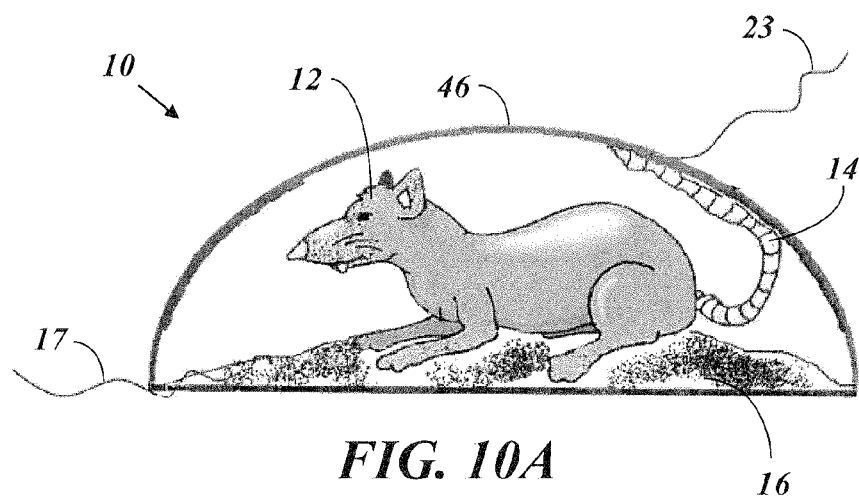
*FIG. 10A*
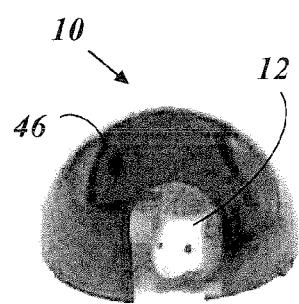 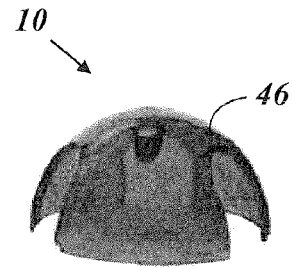
*FIG. 10B*   *FIG. 10C*

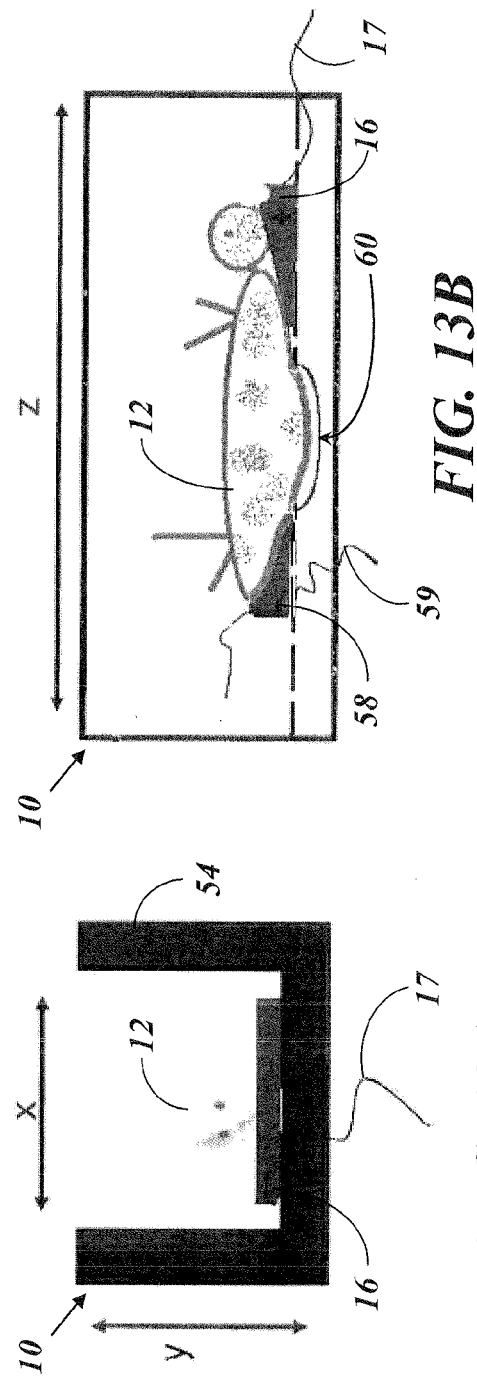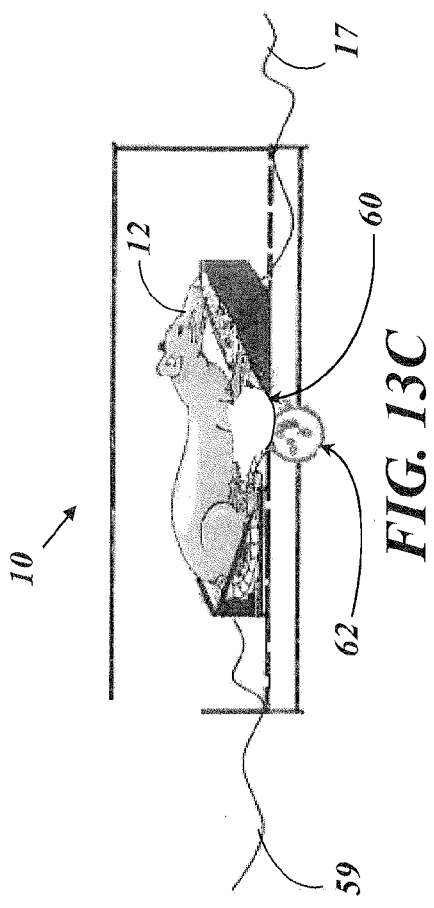
FIG. 13A
FIG. 13B
FIG. 13C

SYSTEMS AND METHODS FOR NON-INVASIVELY RECORDING ECG IN CONSCIOUS AMBULATORY SUBJECTS

RELATED APPLICATIONS

This application claims priority to, and the benefit of, U.S. Provisional Application No. 61/462,001, filed Jan. 26, 2011, for all subject matter disclosed. This application also claims priority to, and the benefit of, U.S. Provisional Application No. 61/462,598, filed Feb. 4, 2011, for all subject matter disclosed. The disclosures of said provisional applications are hereby incorporated by reference in their entireties.

FIELD OF THE INVENTION

The present invention relates to noninvasive measurements of physiological characteristics in mammals. More particularly, the present invention relates to systems and methods for establishing electrical connections in conscious rodents for purposes of recording an electrocardiogram (ECG),

BACKGROUND OF THE INVENTION

Small animals are routinely used in the research setting. It is often of interest to record the electrocardiogram from mice and rats, as well as other rodents such as hamsters and guinea pigs. Given their high level of activity when they are awake, ECGs are often recorded when the animals are under anesthesia. Alternatively, telemetric transmitters are implanted, which communicate wirelessly with receivers, to provide the ECG in conscious awake mice, after they recover from the implantation procedure.

The implants and ancillary recording equipment are expensive, however. One known alternative is to record an ECG in a conscious rodent by placing the animal atop an instrumented platform whereby the ECG signal is detected passively through the underside of their paws. One limitation of this paradigm, however, is the relatively short window of time during which the ECG recordings are made. For example, mice or other rodents occasionally escape from the elevated platform, thereby breaking the electrical connection and evading measurement.

SUMMARY

There is a need, therefore, for methods and devices for recording the ECG in conscious rodents that enable ECG recordings for longer periods of time, without use of implants or surgery. The present invention is directed toward solutions to address this and other needs, in addition to having other desirable characteristics that will be appreciated by one of skill in the art upon reading the present specification.

In accordance with an example embodiment of the present invention, a chamber device for non-invasively acquiring an electrocardiogram (ECG) of a conscious subject having a tail can include a first electrically conductive platform for establishing an electrical connection with the subject at a first location of the subject other than the tail. The first electrically conductive platform can be configured to be coupled to ECG recording equipment. An electrical conducting device independent from the electrically conductive platform for establishing an electrical connection with the tail of the subject can be included in the chamber and can be configured to be coupled to the ECG recording equipment. The electrical conducting device can be in a fixed position relative to the electrically conductive platform, and the electrical conducting device can be positioned in such a way as to contact the tail of the subject during motion of the subject.

In accordance with further embodiments of the present invention, the electrical conducting device can include a second electrically conductive platform. The second electrically conductive platform can be situated beside the first electrically conductive platform. The electrical conducting device can include a region of electrically conductive material situated in such a way as to form a perimeter around the first electrically conductive platform. The region of electrically conductive material can be substantially level with or elevated above the first electrically conductive platform. The chamber electrical conducting device can include a region of electrically conductive material situated on or forms one or more housing elements forming the chamber. The region of electrically conductive material can be situated on or can form one or more walls of the chamber. The region of electrically conductive material can be situated on or can form a dome or ceiling of the chamber. The electrical conducting device can include a plurality of electrically conductive posts extending through a plurality of holes in the first electrically conductive platform. One or more of a second electrically conductive platform or an aqueous reservoir can be situated below the first electrically conductive platform. The plurality of electrically conductive posts can be coupled with the second electrically conductive platform or the aqueous reservoir. The subject can be a mammal or a rodent.

In accordance with another example embodiment of the present invention, a chamber device for non-invasively acquiring an electrocardiogram (ECG) of a conscious subject having a tail can include a first electrically conductive platform for establishing an electrical connection with the subject at a first location of the subject other than the tail. The first electrically conductive platform can be configured to be coupled to ECG recording equipment. An electrical conducting device can be included that is independent from the electrically conductive platform for establishing an electrical connection with the tail of the subject. The electrical conducting device can be configured to be coupled to the ECG recording equipment. The electrical conducting device can be movable relative to the electrically conductive platform. The electrical conducting device can be positioned in such a way as to contact the tail of the subject.

In accordance with further embodiments of the present invention, the electrical conducting device can include a moveable electrode. The movable electrode can be coupled to a ferrite or magnetic material. An access opening can be included in the chamber device. The chamber device can include a positioning tool coupled to the electrode and extending through the access opening. The electrical conducting device can include a ringlet configured to fasten around the tail of the subject. The electrical conducting device can include an electrically conductive food element and an electrically conductive conduit situated in the electrically conductive food element. The electrical conducting device can include a second electrically conductive platform that is movable relative to the first electrically conductive platform. The first electrically conductive platform and the second electrically conductive platform can be separated by an adjustable amount of space. The subject can be a neonatal subject and the chamber device can form a channel sized to substantially maintain an orientation of the neonatal subject. The chamber device further can include a heating element, e.g., for heating the neonatal subject.

BRIEF DESCRIPTION OF THE FIGURES

These and other characteristics of the present invention will be more fully understood by reference to the following detailed description in conjunction with the attached drawings, in which:

FIGS. 3A and 3B are perspective views of the chamber of FIG. 1 further including a moveable electrode coupled to a tool, according to example embodiments of the present invention;

FIG. 10A is a cross-sectional side view of the chamber of FIG. 1 further including an electrically conductive dome forming a ceiling of the chamber, according to example embodiments of the present invention;

FIGS. 10B and 10C are perspective views of the chamber of FIG. 10A, according to aspects the present invention;

FIGS. 13A and 13B are a front view and a side view, respectively, of the chamber of FIG. 1 adapted for neonatal subjects, according to example embodiments of the present invention;

FIG. 13C is a perspective view of the chamber of FIGS. 13A and 13B further including a heating element, according to example embodiments of the present invention;

DETAILED DESCRIPTION

Figure 1:
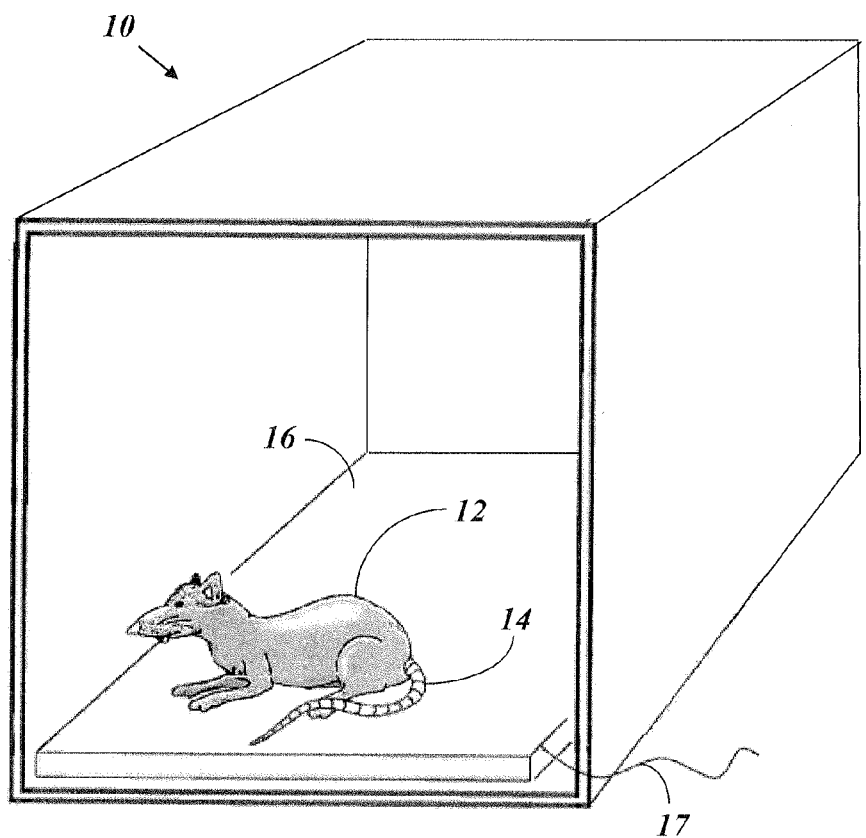
FIG. 1 is a perspective view of a chamber with an electrically conductive platform for measuring an ECG, according to example embodiments of the present invention.

Certain illustrative embodiments of the present invention are based on the novel observation that an electrocardiogram (ECG) in a conscious moving rodent can be detected via the tail of the animal (e.g., using passive mechanisms to initiate contact), and another (e.g., a single additional) portion of the subject's anatomy, preferably one forward of the heart, such as a forepaw. It is known to those of skill in the art that to render an ECG, at least two points of contact must be established on one of two sides (either base to axis, or dorsal to ventral) of the heart. One point of contact is considered positive, and another point of contact is considered negative.

The present inventors have further observed that when one point of contact is the tail, the entire remainder of the subject rostral to the heart, or portions thereof, can contribute to, or be co-incident with, the second point of contact. As such, an electrically conductive platform upon which a rodent rests or explores can form the first electrode, and an electrical contact made with a portion of the tail can form the second electrode. As such, certain illustrative embodiments described herein provide a cage or chamber that promotes independent contact between an electrode contiguous to the tail as the rodent explores the cage or chamber. Furthermore, the cage or chamber establishes an electrical connection with some anatomical portion of the rodent caudal to the heart, such as one or more of the subject's belly, chest, paw, hand, limb, head, ears, or mouth (e.g., or a portion thereof). The chamber further is configured to promote contact between the tail and the second point of contact such that the ECG can be recorded when the established electrical connections at the positive ("+") and negative ("−") electrodes are relayed to and resolved by the appropriate bioamplification and ECG recording instrumentation. The physics underlying the biopotential of the heart, and the electrical recording mechanisms used to perform such measurements, are well understood and known to those of skill in the art.

Notably, embodiments of the present invention provide novel methods, systems, and apparatuses for establishing the points of contact between the positive ("+") and negative ("−") recording sites on the subject that provide greater convenience, increased reliability, and reduced invasiveness to the subject.

FIGS. 1 through 16, wherein like parts are designated by like reference numerals throughout, illustrate example embodiments of systems and methods for noninvasively recording ECGs in conscious animals, according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

FIG. 1 depicts a chamber 10 from a perspective view, according to an example embodiment of the present invention. A front-facing wall of the chamber 10 is depicted as transparent, for purposes of illustration and clarity. One of skill in the art will appreciate that many different types of materials can be used to form the chamber 10. The present invention is not limited to the illustrative examples provided herein. The chamber 10 can be configured for anesthetizing a subject with a halogenated gas, such as isoflurane. The chamber 10 further can be configured for recording the ECG in the subject while it is still conscious, e.g., as it succumbs to the sedative effects of the isoflurane. As would be appreciated by one of skill in the art, the chamber 10 can include an inlet (not shown) for the receiving of the halogenated gas, and an outlet (not shown) for allowing the gas to exit the chamber 10, e.g., coupled to a scavenging reservoir. A subject 12 (e.g., a mouse) is depicted as being situated within the chamber 10. Given that the subject 12 is typically quite active when awake, particularly when placed inside a new environment, the position of a tail 14 of the subject 12 may be unpredictable within the chamber 10.

The chamber 10 is instrumented with one or more mechanisms for recording the ECG from the tail 14 (or another position rearward or caudal to the heart) and from points forward of the tail 14 (e.g., preferably forward of or rostral to the heart). For example, a platform 16 can be included, e.g., which forms all or part of a floor of the chamber 10. The platform 16 includes a surface that is electrically conductive (e.g., that is formed of electrically conductive material). Thus, an electrical connection is established and substantially maintained with the subject 12 once it is placed atop the platform 16 and enabled to freely move about. Specifically, the electrical connection is established between the electrically conductive surface of the platform 16 and any points of the subject 12 in contact with the surface of the platform 16. The platform 16 can be selectively removable from and replaceable within the chamber 10, e.g., to enable convenient disposal and/or replacement with an equivalent such platform 16. The platform 16 is coupled to ECG recording equipment by a conduit 17 (e.g., an electrical wire), thereby allowing electrical signals generated at the platform 16 due to physical contact with the subject 12 to be transferred to the ECG recording equipment.

As just some non-limiting and illustrative examples, the surface of the platform 16 can be formed of a rigid metal, such as tin, silver, bronze, gold, platinum, or any of its alloys and combinations thereof. In some embodiments, the platform/floor is formed of an aqueous but firm medium such as pizza dough or marshmallow. In yet other embodiments, the platform is formed of a moist cotton fiber element (e.g., with a thickness of about 0.09 inches or less). In some embodiments, the platform 16 is formed of moistened paper. In other embodiments, the platform 16 is formed of wood particulate matter, moistened sufficiently to provide electrical conductivity satisfactory for recording an ECG. In illustrative embodiments, the platform 16 is sized and shaped to allow the subject 12 to freely explore its surface. For example, the platform 16 can, in fact, be a preferred place of habitation for the subject 12.

Figures 2A, 2B:
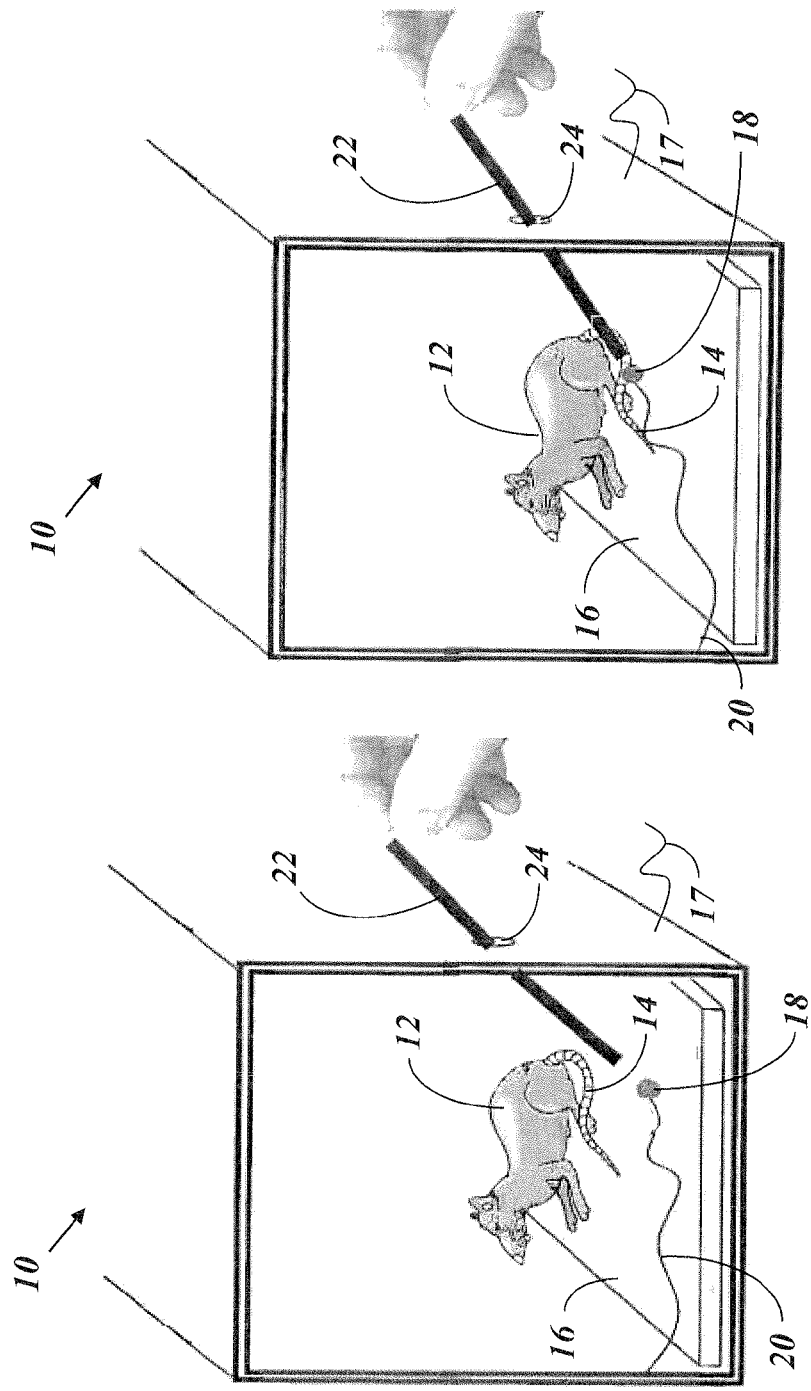
FIGS. 2A and 2B are perspective views of the chamber of FIG. 1 further including a moveable electrode, according to example embodiments of the present invention.

Turning now to FIGS. 2A and 2B, a movable electrode 18 can be situated within the chamber 10 of FIG. 1. The movable electrode 18 can be positioned and repositioned (e.g., manually or automatically) to physically contact the tail 14 of the subject 12, thereby establishing an electrical connection and providing the second point of electrical contact required for a successful ECG measurement. The movable electrode 18 can be coupled to a conduit 20, such as a conductive wire, that connects to the ECG recording equipment (not shown). Movement of the electrode 18 can be achieved by human or mechanical means, e.g., performed external to the chamber 10. In the example embodiment of FIGS. 2A and 2B, a long slender tool 22 selectively enters the chamber 10 from an opening 24 leading from within the chamber 10 to an environment outside of the chamber 10. Thus, external manipulation of the tool 22 causes a distal tip of the tool 22 situated within the chamber 10 to move the movable electrode 18 into contact with the tail 14 of the subject 12.

Alternatively, the electrode 18 can be included in the tool 22. For example, FIGS. 3A and 3B depict embodiments in which the electrode 18 is affixed to the distal end of the tool 22 (e.g., positioned in the chamber 10). The length of the tool 22 thus can house the electrically conductive conduit 20 coupling the electrode 18 to the ECG recording equipment (not shown). The proximal end of the tool 22 can be coupled to ECG recording equipment, thereby enabling an electrical signal generated at the tail 14 to travel from the electrode 18 at the distal end of the tool 22 through the conduit to the ECG recording equipment, as would be appreciated by one of skill in the art. Thus, in the example embodiments of FIGS. 3A and 3B, the platform 16 forms a first point of electrical contact and the electrode 18 forms a second point of electrical contact, thereby enabling a measurement of an ECG in the subject 12 to be taken. As depicted in FIG. 3A, the opening 24 can be situated in a side wall of the chamber 10. Alternatively, as depicted in FIG. 3B, the opening 24 can be situated in a ceiling of the chamber 10, such that the tool 22 is suspended within the chamber 10 and positioned (e.g., manually or automatically) to contact the tail 14 of the subject 12.

Figure 4A:
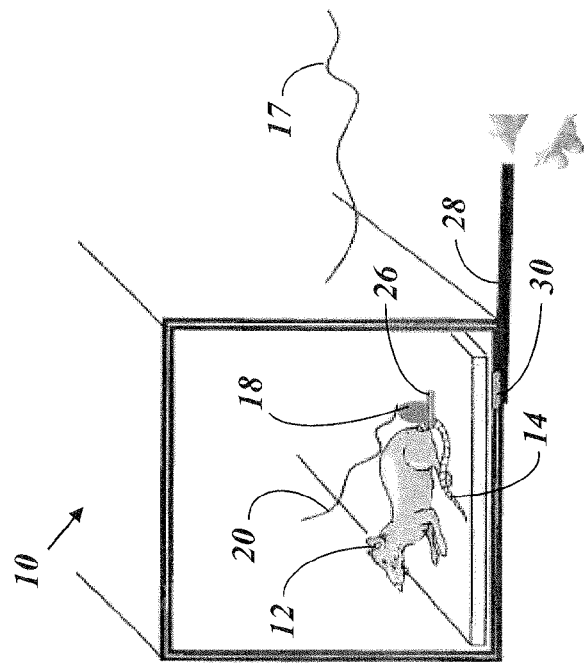
FIGS. 4A and 4B are perspective views of the chamber of FIG. 1 further including a moveable electrode coupled to a ferrite or magnetic material, according to example embodiments of the present invention.
Figure 4B:
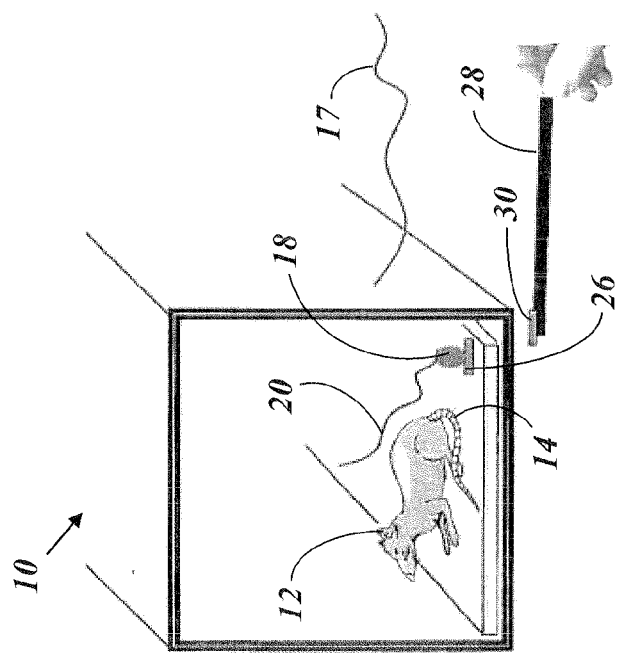

FIGS. 4A and 4B depict yet other embodiments of the chamber 10 of FIG. 1 according to the present invention. In the example embodiments of FIGS. 4A and 4B, the movable electrode 18 (e.g., of FIGS. 3A and 3B) is situated within the to chamber 10 and is coupled to or incorporated into a ferrite or magnetic material 26. The ferrite or magnetic material 26 is attracted to a ferrite or magnetic articulator 28 having a ferrite or magnetic distal end situated exterior to the chamber 10. Thus, movement of the ferrite or magnetic articulator 28 exterior to the chamber 10 affects movement of the movable electrode 18 internal to the chamber 10. In illustrative embodiments, the ferrite or magnetic material 26 has a polarity that is opposite from a polarity of the ferrite or magnetic articulator 28, such that motion by the ferrite or magnetic articulator 28 is roughly "paralleled" by the ferrite or magnetic material 26.

In such example embodiments as those of FIGS. 2A through 4B, the movable electrode 18 preferably establishes an electrical connection by contacting the subject 12 at a position rearward (e.g., caudal to) the heart (e.g., the tail 14), and the platform 16 preferably establishes an electrical connection by contacting the subject 12 at a position forward of (e.g., rostral to) the heart of the subject 12.

Figure 5A:
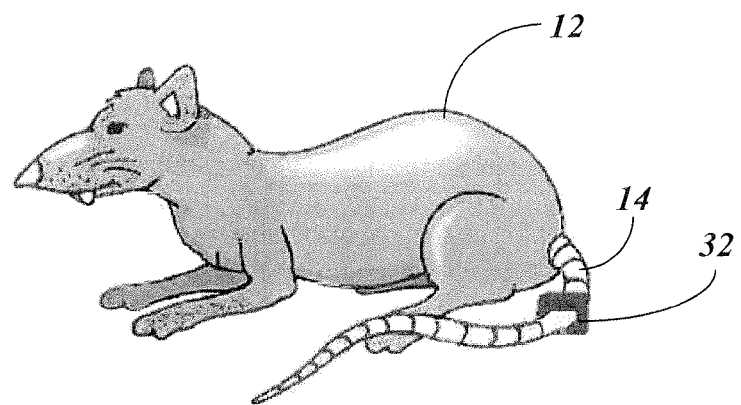
FIG. 5A is a perspective view of a subject with an electrically conductive ringlet positioned on a tail of the subject, according to aspects of the present invention.
Figure 5B:
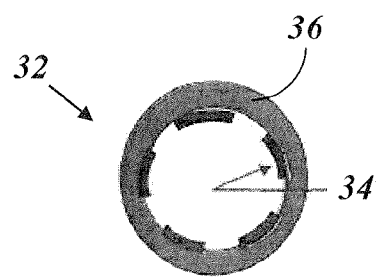
FIG. 5B is a close-up view of the ringlet of FIG. 5A, according to aspects of the present invention.

FIGS. 5A and 5B depict an example embodiment of a ringlet 32 for inclusion in the chamber 10 depicted in FIG. 1. As depicted in FIG. 5A, the ringlet couples with the subject 12, thereby establishing the second electrical connection required to take the ECG measurement. Specifically, the ringlet 32 can slip over and fasten to the tail 14 of the subject 12. In the example embodiment of FIG. 5B, the ringlet 32 includes a conductive ring 36 coupled by a conduit (not shown) to ECG recording equipment (not shown). In certain embodiments adapted for mice, the inside diameter of the ringlet 32 can be about 0.2 inches or less. The inside surface of the ringlet 32 is coated with an adhesive material 34 that is electrically conductive, so as to assist in establishing a strong electrical connection with the tail 14. The adhesive material 34 can be a material that is not noxious to the subject 12, such as one or more of an organic sucrose-based substance (e.g., molasses), peanut butter, marshmallow, or corn syrup. One of skill in the art will appreciate yet other types of adhesive materials 34 upon reading the specification. All such alternatives and modifications are contemplated within the scope of the present invention.

In further embodiments according to the present invention, the ringlet 32 of FIGS. 5A and 5B additionally includes a ferrite or magnetic material (e.g., coupled to the conductive ring 36). In such further embodiments, the ferrite or magnetic articulator 30 of FIGS. 4A and 4B can included. Due to the magnetic forces between the ferrite or magnetic material of the ringlet 32 and the ferrite or magnetic articulator 30, the ferrite or magnetic articulator 30 enables remote manipulation of the ringlet 32. For example, the ferrite or magnetic articulator 30 can be used to assist in remotely positioning the ringlet 32 onto the tail 14 of the subject 12 without requiring a researcher or worker to physically reach into the chamber 10.

In the example embodiment of FIGS. 5A and 5B, the ringlet 36 establishes an electrical connection by contacting the subject 12 at the tail 14, and the platform 16 preferably establishes an electrical connection by contacting the subject 12 at a position forward of (e.g., rostral to) the heart of the subject 12.

Figure 6:
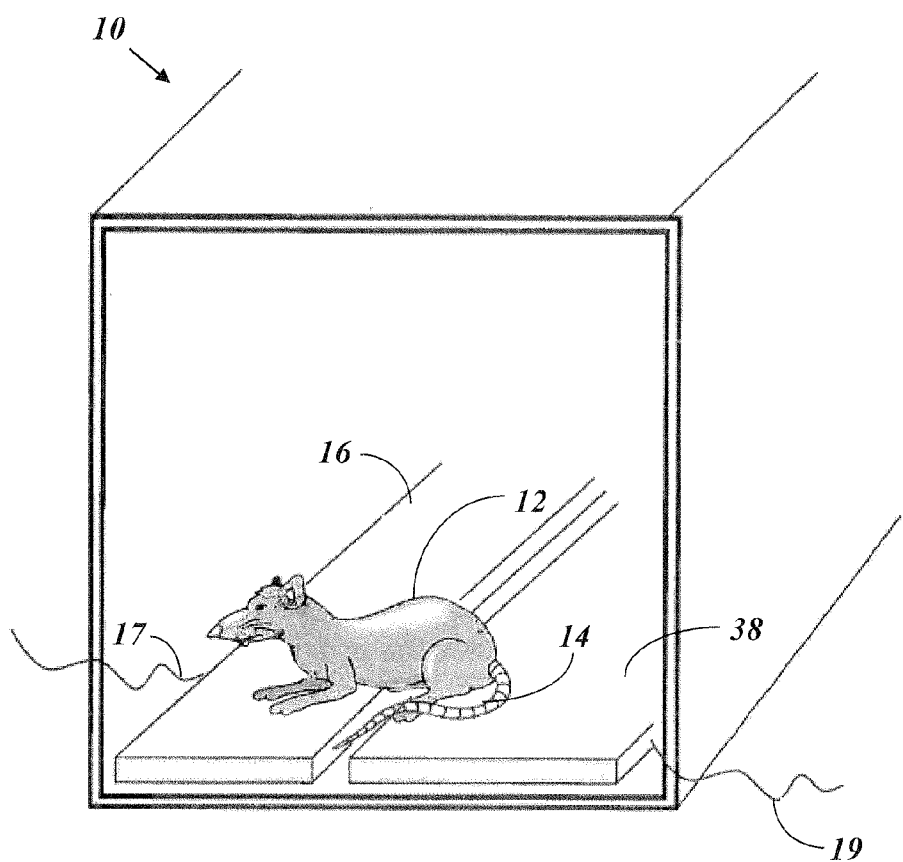
FIG. 6 is a perspective view of the chamber of FIG. 1 further including a second electrically conductive platform, according to example embodiments of the present invention.

FIG. 6 depicts another example embodiment of the chamber 10 of FIG. 1 according to the present invention. In the example embodiment of FIG. 6, a second electrically conductive platform 38 is included that is independent from the first platform 16. The second platform 38 is coupled to ECG recording equipment (not shown) by a conduit 19 (e.g., an electrical wire). Thus, the ECG measurement is rendered when two independent points of contact are established between the subject 12 and the two platforms 16, 38. For example, the tail 14 or a hind paw can be in contact with the second platform 38, while a forepaw can be in contact with the first platform 16.

In the example embodiment of FIG. 6, the second platform 38 can establish an electrical connection by contacting the subject 12 at a position rearward (e.g., caudal to) the heart (e.g., the tail 14), and the first platform 16 can establish an electrical connection by contacting the subject 12 at a position forward of (e.g., rostral to) the heart of the subject 12. Alternatively, the first platform 16 can establish an electrical connection by contacting the subject 12 at a position rearward (e.g., caudal to) the heart (e.g., the tail 14), and the second platform 38 can establish an electrical connection by contacting the subject 12 at a position forward of (e.g., rostral to) the heart of the subject 12.

Figure 7:
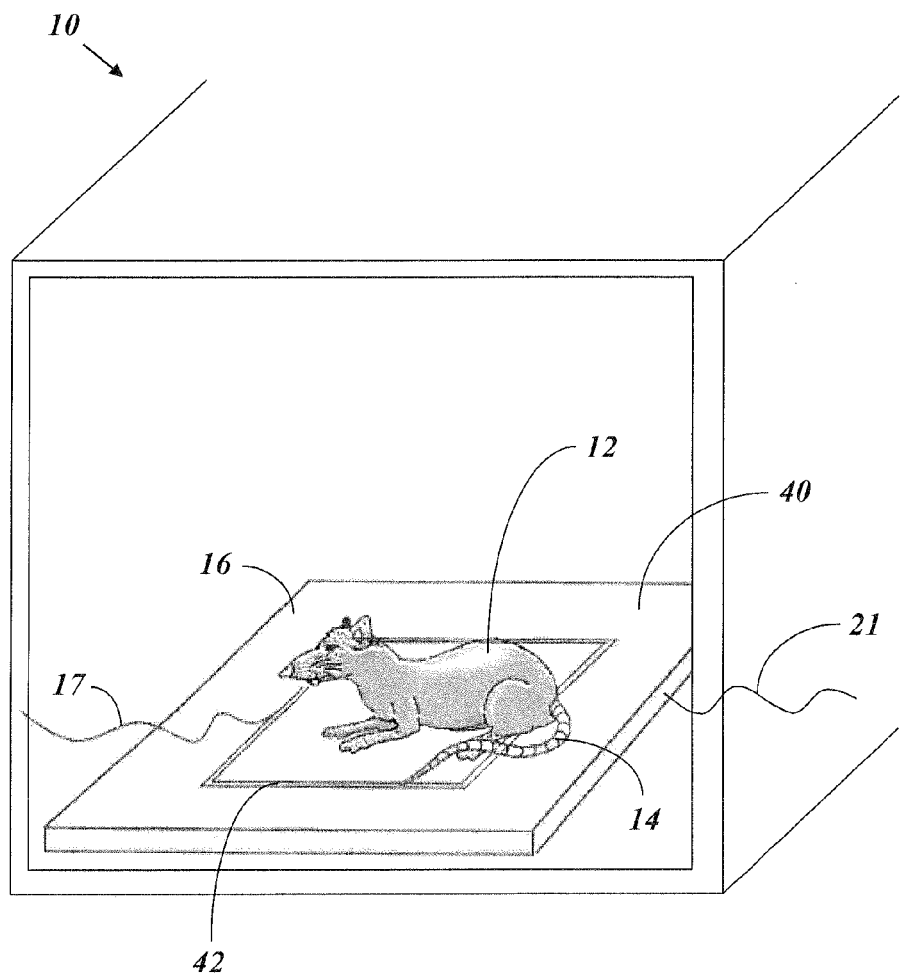
FIG. 7 is a perspective view of the chamber of FIG. 1 further including an electrically conductive region around the platform, according to example embodiments of the present invention.

FIG. 7 depicts another embodiment of the chamber 10 according to the present invention, which includes a region of conductive material 40 that forms an electrically conductive perimeter around the platform 16. The platform 16 can be shaped and sized to provide a primary habitat for the subject 12. The region of conductive material 40 can be shaped and sized to increase the likelihood of the tail 14 contacting the region of conductive material 40 as the subject 12 resides on or explores the platform 16. In the example embodiment of FIG. 7, a non-conductive zone 42 separates the region of conductive material 40 from the platform 16, such that the ECG measurement is not obfuscated by contact between the positive and the negative connections. The region of conductive material 40 is coupled to ECG recording equipment (not shown) by a conduit 21 (e.g., an electrical wire).

In the example embodiment of FIG. 7, the region of conductive material 40 is situated around the platform 16, e.g., forming a portion of a floor of the chamber 10. Furthermore, in the example embodiment of FIG. 7, the region of conductive material 40 and the platform 16 are at substantially the same height relative to one another. The region of conductive material 40 can be formed of a solid or slush-like material, or can be formed of a volume of aqueous solution surrounding the platform 16.

Figure 8:
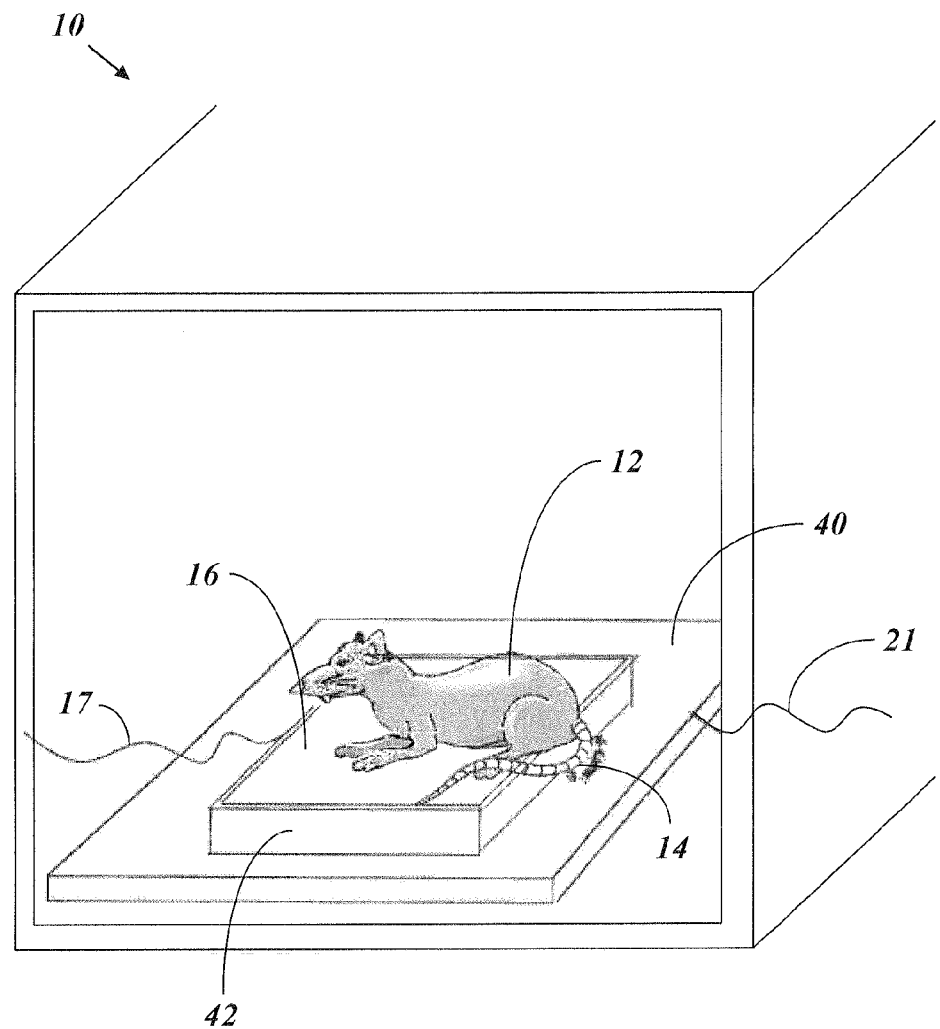
FIG. 8 is a perspective view of the chamber of FIG. 7, further wherein the platform is elevated relative to the electrically conductive region, according to example embodiments of the present invention.

In certain embodiments according to the present invention, the platform 16 is elevated relative to the region of conductive material 40. For example, FIG. 8 depicts an alternative embodiment of the chamber 10 of FIG. 1 according to the present invention, in which the platform 16 is slightly elevated above the perimeter a by height x. In illustrative embodiments, the height x can be equal to $0 < x < Y$ inches, where Y is selected such that the tail 14 of the subject 12 tends to be in contact with the region of conductive material 40 due to the natural force of gravity. Furthermore, the value of Y can be selected such that the tail 14 of the subject 12 tends, for the most part, to be not contiguous (e.g., not in contact) with the platform 16. Said differently, in the example embodiment of FIG. 8, the value of Y is selected such that a distal portion of the tail 14 of the subject 12 naturally gravitates towards the region of conductive material 40. For example, for mice, the value of Y can be equal to about 0.5 inches. As another example, for rats, the value of Y can be equal to about 1.0 inch.

Figure 9:
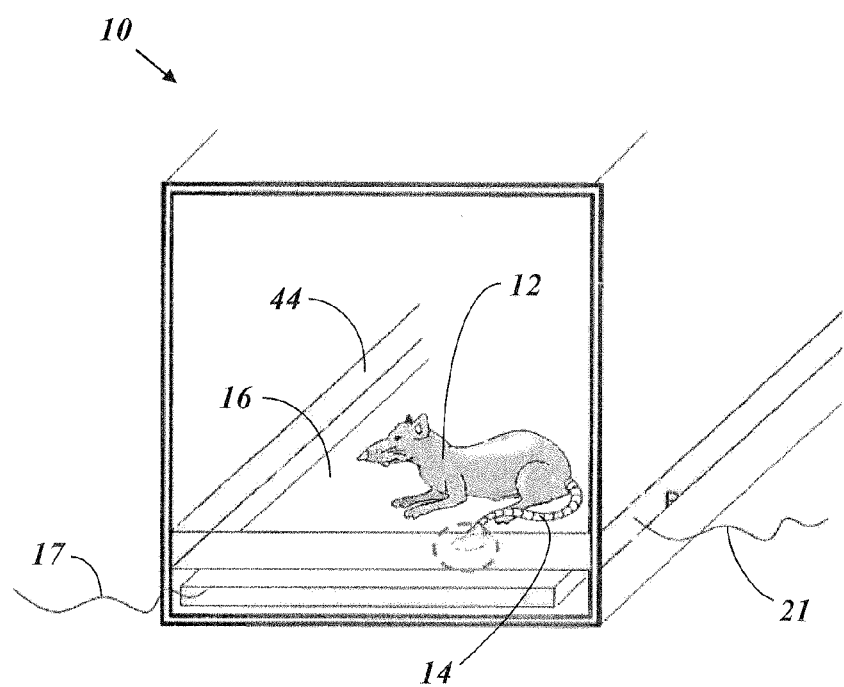
FIG. 9 is a perspective view of the chamber of FIG. 1 further including an electrically conductive region situated on walls of the chamber, according to example embodiments of the present invention.

In the example embodiments of FIGS. 7 and 8 that include the region of conductive material 40, the region of conductive material 40 generally forms a portion of a floor of the chamber 10 and is horizontally flat (e.g., either at the same elevation or at a different elevation as the platform 16). Alternatively, the region of conductive material 40 can be slanted/sloped, e.g., such that it meets the platform 16 at an angle. As yet further alternatives, the region of conductive material 40 can be situated elsewhere besides as a floor. For example, the region of conductive material 40 can be situated on and/or can form walls of the chamber 10 (or portions thereof). For example, FIG. 9 depicts an example embodiment in which the region of conductive material 40 forms a swath of electrically conductive material along the bottom portion of interior walls of the chamber 10. In the example embodiment of FIG. 9, the interior walls form a rectangular or square shape. As with previous embodiments, the region of conductive material 40 is coupled to ECG recording equipment (not shown) by the conduit 21. When a portion of the tail 14 of the subject 12 engages the walls of the chamber 10, a second electrical connection is established, thereby allowing an ECG to be rendered.

In such example embodiments as those of FIGS. 7 through 9, the region of conductive material 40 preferably establishes an electrical connection by contacting the subject 12 at a position rearward (e.g., caudal to) the heart (e.g., the tail 14), and the platform 16 preferably establishes an electrical connection by contacting the subject 12 at a position forward of (e.g., rostral to) the heart of the subject 12.

It is understood that while many chambers and cages for rodents are square or rectangular, any shaped volume for the chamber 10 can be used, such as a sphere, hemisphere, or triangular shaped chamber.

For example, FIGS. 10A through 10C depict another example embodiment of the chamber 10 according to the present invention. In the example embodiment of FIG. 10A, the chamber 10 is dome shaped, such as the dome shaped shelter commonly in use for enriching laboratory animal housing (e.g., the Mouse Igloo® proffered by BioServ, of Frenchtown, N.J.). As with previous embodiments, the electrically-conductive platform 16 can constitute the first point of establishing contact. An electrically conductive dome 46 forming the ceiling can be included in the chamber 10 to provide a second point of contact with the subject 12, whereby an electrical connection is established between the tail 14 of the subject 12 as it contacts the dome 46. As just one illustrative and non-limiting example, the dome 46 can include electrically conductive elements disposed therein. Accordingly, as with previous embodiments, the paws and/or other anatomy of the subject 12 contacting the platform 16 (e.g., in this case, a floor or ground element) establish an electrical connection enabling an ECG to be measured in the subject 12.

In accordance with one example embodiment, the dome 46 includes a surface lining or coating of an electrically conductive material on an interior face thereof. For example, the electrically conductive material can include tin, silver, bronze, gold, platinum, or any of its alloys and combinations thereof. Other conductive linings or coatings that can be included in the dome 46 can include eggshell, other organic pastes or coatings, or moistened paper. One of skill in the art will appreciate a variety of other suitable linings or coatings that can be used. The present invention is in no way limited to the illustrative examples provided herein. The extent or area of the dome 46 occupied by the surface lining or coating can be selected to maximize the opportunity for establishing an electrical connection with the tail 14 of the subject 12. Mechanisms for electrically connecting the coating or lining (e.g., a conduit 23) to ECG recording equipment (not shown) are well understood to those of skill in the art, and can be included in the chamber 10, to enable transmission of an electrical signal at the dome 46 to ECG recording equipment.

In some such embodiments as that depicted in FIGS. 10A through 10C, a small reservoir of water (not shown) is established atop of the chamber 10 that, via hydrostatic gradient or other suitable mechanism, continues to moisten the coating or lining below the reservoir (not shown). In this manner, the reservoir can provide moisture to paper or other absorbent material forming the coating or lining, thereby preventing the coating or lining from becoming too dry to conduct an electrical signal.

In the example embodiments of FIGS. 10A through 10C, the dome 46 preferably establishes an electrical connection by contacting the subject 12 at a position rearward (e.g., caudal to) the heart (e.g., the tail 14), and the platform 16 preferably establishes an electrical connection by contacting the subject 12 at a position forward of (e.g., rostral to) the heart of the subject 12.

Figure 11A:
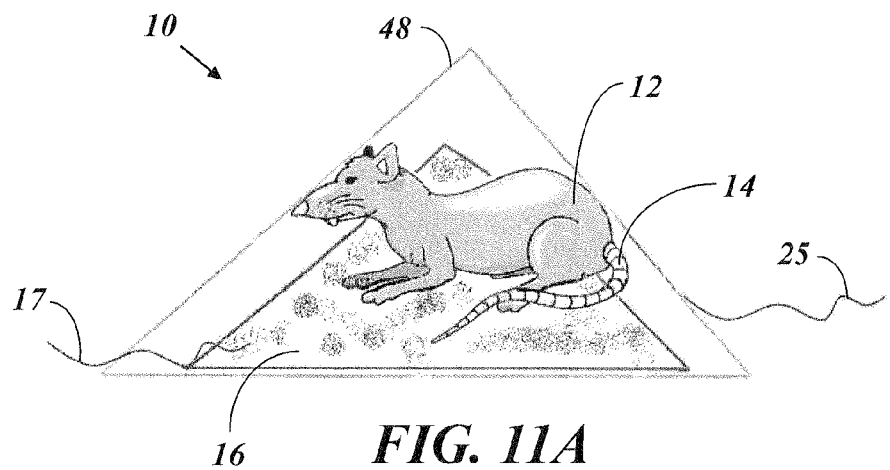
FIG. 11A is a cross-sectional side view of the chamber of FIG. 1 further including electrically conductive portions, according to example embodiments of the present invention.
Figure 11B:
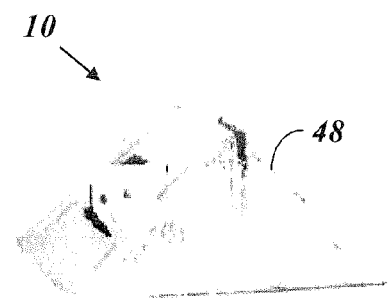
FIGS. 11B and 11C are perspective views of the chamber of FIG. 11A, according to aspects the present invention.
Figure 11C:
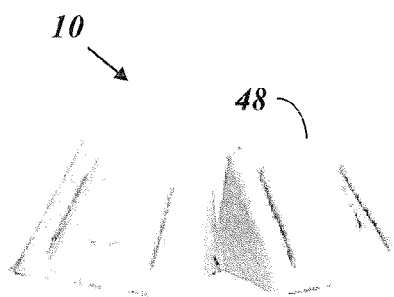

FIGS. 11A through 11C depict an example embodiment in which portions 48 of the chamber 10 itself (e.g., walls and/or ceilings) are made from a 100% virgin wood pulp, cotton fiber, paper, cardboard or another electrically conductive material, such that points on the chamber 10 form a second point of contact for establishing an electrical connection that, in combination with the electrical connection established at the platform 16, allow an ECG measurement to be recorded. In such embodiments, the platform 16 of the chamber 10 can be positioned to not be electrically contiguous with the electrically conductive portions 48 of the chamber 10 (e.g., walls and/or ceiling), such that two unique points of electrical contact can be established (e.g., a first between the platform 16 and points ventral to the subject 12, and a second between the electrically conductive portions 48 of the chamber 10 and the tail 14 and/or points dorsal to the subject 12). Additionally, mechanisms for electrically connecting the electrically conductive portions 48 of the chamber 10 (e.g., walls and/or ceiling) to ECG recording equipment can be included (e.g., a conduit 25), as would be readily appreciated by one of skill in the art.

In some such embodiments as that depicted in FIGS. 11A through 11C, mechanisms may be included to maintain suitable levels of moisture in the electrically conductive portions 48 of the chamber 10 (e.g., walls and/or ceiling) and/or the platform 16 to enable electrical conductivity. For example, a small reservoir of water (not shown) can be provided atop the chamber 10 that, via hydrostatic gradient or other means, continues moisten the chamber 10 below the reservoir, whereby the absorbent material attracts the moisture to prevent it from becoming too dry to be electrically conductive. Additionally, mechanisms for electrically connecting the electrically conductive portions 48 of the chamber 10 (e.g., walls and/or ceiling) to ECG recording equipment can be included (e.g., a conduit 25), as would be readily appreciated by one of skill in the art.

In the example embodiments of FIGS. 11A through 11C, the electrically conductive portions 48 preferably establish an electrical connection by contacting the subject 12 at a position rearward (e.g., caudal to) the heart (e.g., the tail 14), and the platform 16 preferably establishes an electrical connection by contacting the subject 12 at a position forward of (e.g., rostral to) the heart of the subject 12.

Figure 12:
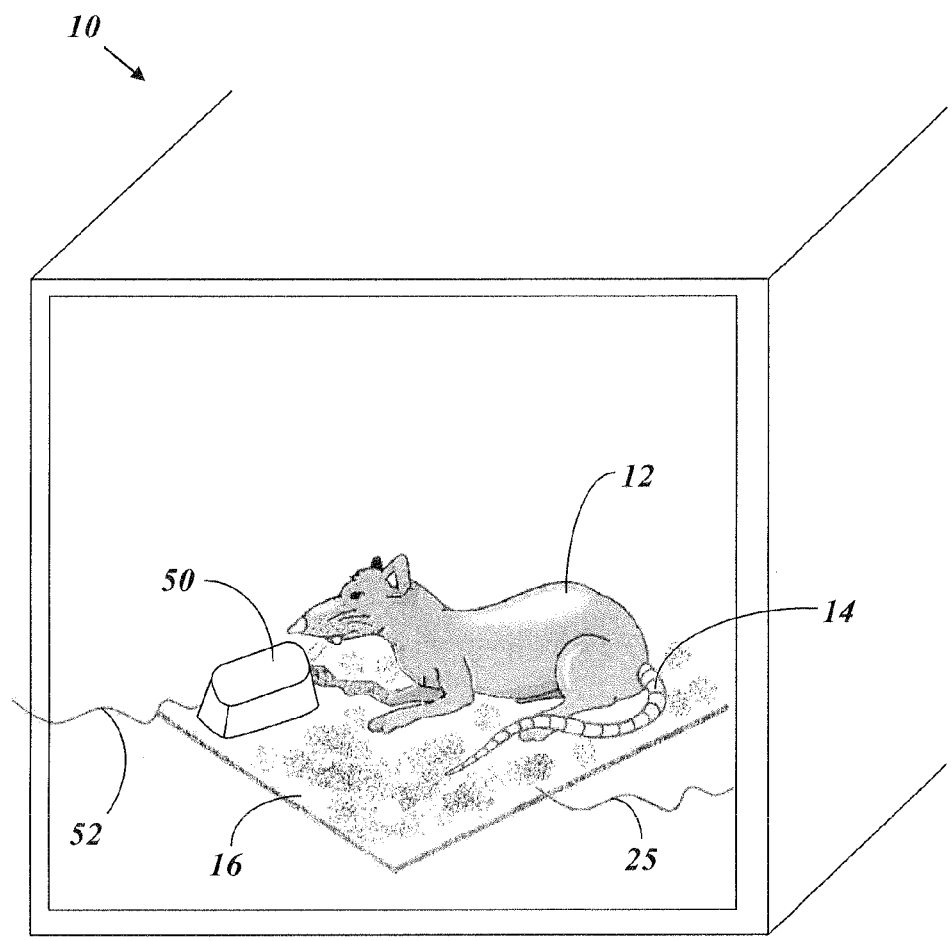
FIG. 12 is a perspective view of the chamber of FIG. 1 further including a food element configured to establish an electrical connection with the subject, according to example embodiments of the present invention.

In other embodiments according to the present invention, a conduit (e.g., an electrical wire) is inserted into a food element to be consumed by the subject 12. For example, FIG. 12 depicts an example embodiment of the chamber 10 further including such a food element 50. The food element 50 is coupled by a conduit 52 to ECG recording equipment (not shown). More specifically, the conduit 52 is inserted into the food element 50 in such a way that the food element effectively becomes an electrode for establishing an electrical connection with the subject 12 that, in addition to the electrical connection established at the platform 16 during handling or mastication of the food element 50, allows an ECG to be recorded. For example, the ECG can be established between a portion of the subject 12 that is contiguous with the food element 50 (e.g., a forelimb, a tongue, etc.) and other parts of the subject 12 caudal to the heart (e.g., a hind limb, a tail, etc., as previously described herein).

In the example embodiment of FIG. 12, the food element 50 preferably establishes an electrical connection by contacting the subject 12 at a position forward of (e.g., rostral to) the heart of the subject 12, and the platform 16 preferably establishes an electrical connection by contacting the subject 12 at a position rearward (e.g., caudal to) the heart, such as the tail 14.

FIGS. 13A through 13C depict yet a further example embodiment of the chamber 10 according to the present invention. As depicted in FIGS. 13A and 13C, the chamber 10 can be adapted for recording ECGs in newly born subjects 12, such as newborn mice, newborn rats, newborn guinea pigs, newborn hamsters, and any other suitable newborn subject. The chamber 10 is configured in such a way as to take advantage of the fact that newborn subjects 12 typically are smaller in size and exhibit relatively low levels of activity, even when conscious.

Continuing with FIGS. 13A and 13C, the chamber 10 can be formed as an elongate channel. As illustrative and non-limiting examples, the channel-like chamber 10 can have a front profile that is generally C-shaped or U-shaped (e.g., with curved and/or sharp edges), as depicted in FIG. 13A. The chamber 10 can have a width of X, can have walls 54 of height Y, and can have a length of Z. As one illustrative and non-limiting example adapted for mice, X can be about 0.3 inches to about 2.0 inches, Y can be about 0 inches to about 1.5 inches, and Z can be about 0.5 inches to about 3.0 inches. In the example embodiments of FIGS. 13A through 13C, the platform 16 is situated nearer to a front end of the chamber 10, and can be electrically conductive by virtue of a positive ECG recording electrode (not shown) situated therein. In the example embodiments of FIGS. 13A through 13C, the platform 16 is configured to establish an electrical connection with the subject 12 at a position on an anterior end of the subject 12. The chamber 10 also includes a second platform 58 at a back end of the chamber 10, which is configured to establish an electrical connection with the subject 12 at a position on a posterior end of the subject 12. For example, the second platform 58 can include a negative ECG recording electrode (not shown) situated therein. Mechanisms (e.g., conduits 17, 59) for electrically connecting the platforms 16, 58 (respectively) to ECG recording equipment can be included, as would be readily appreciated by one of skill in the art.

The neonatal subject 12 is positioned inside the channel-like chamber 10 so that the long axis of the subject 12 is nearly parallel to the long axis of the chamber 10 (e.g., such that the length of the subject 12 is substantially parallel to the length of the chamber 10). A concavity 60 in a floor surface of the chamber 10 between the platforms 16, 58 can be included (as depicted in FIG. 13B) to allow gravity to cause a majority of the body of the subject 12 to fall or dip into the concavity 60. The concavity 60 can be beneficial, e.g., in promoting the neonatal subject 12 to repose on its back. For example, it has been observed by the present inventor that newborn hamsters tend to lie on their backs as if seeking their mother's teats from below.

Furthermore, as a subject 12 ages and becomes able to right itself upon its limbs, the concavity 60 below can be useful in keeping the body of the subject 12 away from the floor, such that the anterior and posterior points of contact on the subject 12 are maintained. Moreover, in some further embodiments, the concavity 60 houses a heating element 62 or a mechanism for detecting diaphragm displacement (not shown) that is co-incident with breathing (e.g., for detection of respiratory rate), as depicted in FIG. 13C.

In the example embodiments of FIGS. 13A through 13C, the walls 54 of the chamber 10 can be sized and positioned to keep the subject 12 relatively within the confines of the chamber 10, thereby maintaining contact of the posterior and anterior portions of the subject 12 with the platforms 16, 58. A non-electrically conductive zone is established between the platforms 16, 58 to maintain distinctness between points of electrical contact, to avoid interfering with the electrical signals used to produce the ECG recording.

In a further embodiment according to the present invention, the chamber 10 can be configured to accommodate differently sized animals. For example the platforms 16, 58 can be movable along the long axis (e.g., length) of the chamber 10, such that the non-conductive zone between the platforms 16, 58 is reduced for small animals and increased for larger animals. For example, each of the platforms 16, 58 can be placed on one or more tracks that allow sliding motion therealong. In another embodiment, the chamber 10 itself can be formed of a front housing element and a rear housing element that are movable relative to each other. The first platform 16 can be situated (e.g., fixedly) in the front housing element and the second platform 58 can be situated (e.g., fixedly) in the rear housing element, such that accommodation of the subject size is accomplished by adjusting the space in between the front and rear housing elements of the chamber 10.

It should be noted that some hairless neonatal animals typically require warmth to maintain good health. The chamber 10 thus can include mechanisms for heating the surfaces of the platforms 16, 58 that are in contact with the animal. In one embodiment, the platforms 16, 58 are electrically conductive by virtue of electrodes situated therein and/or thereon, and the electrodes are made from an organic paste or dough that can be heated (e.g., via a microwave or other suitable heating device). Thus, the electrodes situated in and/or on the platforms 16, 58 maintain a relatively stable temperature for a period of time sufficient for performing ECG recordings.

In accordance with one example embodiment, one or both of the platforms 16, 58 are made from balsam wood or another organic solid that can be moistened to enhance electrical conductivity. In another embodiment, a heater is attached to the chamber 10 to provide heat to the chamber 10 and the platforms 16, 58 (e.g., the electrodes situated therein and/or thereon). In one embodiment, the heating element is a heating rod of about 0.5 inches diameter and about 2.0 inches or less in length. The heating rod can be inserted below and across the chamber 10, such that it beneath a majority of the subject 12. In one embodiment, the heating rod is positioned inside the concavity 60 in the floor of the chamber 10, e.g., depicted in FIGS. 13B and 13C. In another embodiment, the heating source derives its electrical power from a computer, such as via a USB type of connection available on most computers, or any other suitable electrical source on a computer.

In one embodiment the chamber 10 is constructed of one or more of paper, cardboard, or wood pulp. Additionally, paper, cardboard, and/or wood pulp can be used as nesting material enclosing the neonatal subject 12, such that the neonatal subject 12 can be transferred to and from its cage to the chamber 10 with minimal human contact.

In embodiments provided herein, the chamber 10 can be contained within a larger chamber, cage, or housing that also contains ECG recording equipment for rendering ECGs based on electrical connection established with the subject 12 in the chamber 10. In this way, for example, ECGs can be recorded noninvasively in conscious laboratory mice within the mice's home cage without the need for telemetric implants or restraint.

In such example embodiments as those depicted in FIGS. 13A through 13C, the first platform 16 preferably establishes an electrical connection by contacting the subject 12 at a position forward of (e.g., rostral to) the heart of the subject 12, and the second platform 58 preferably establishes an electrical connection by contacting the subject 12 at a position rearward (e.g., caudal to) the heart, such as the tail 14.

Figure 14A:
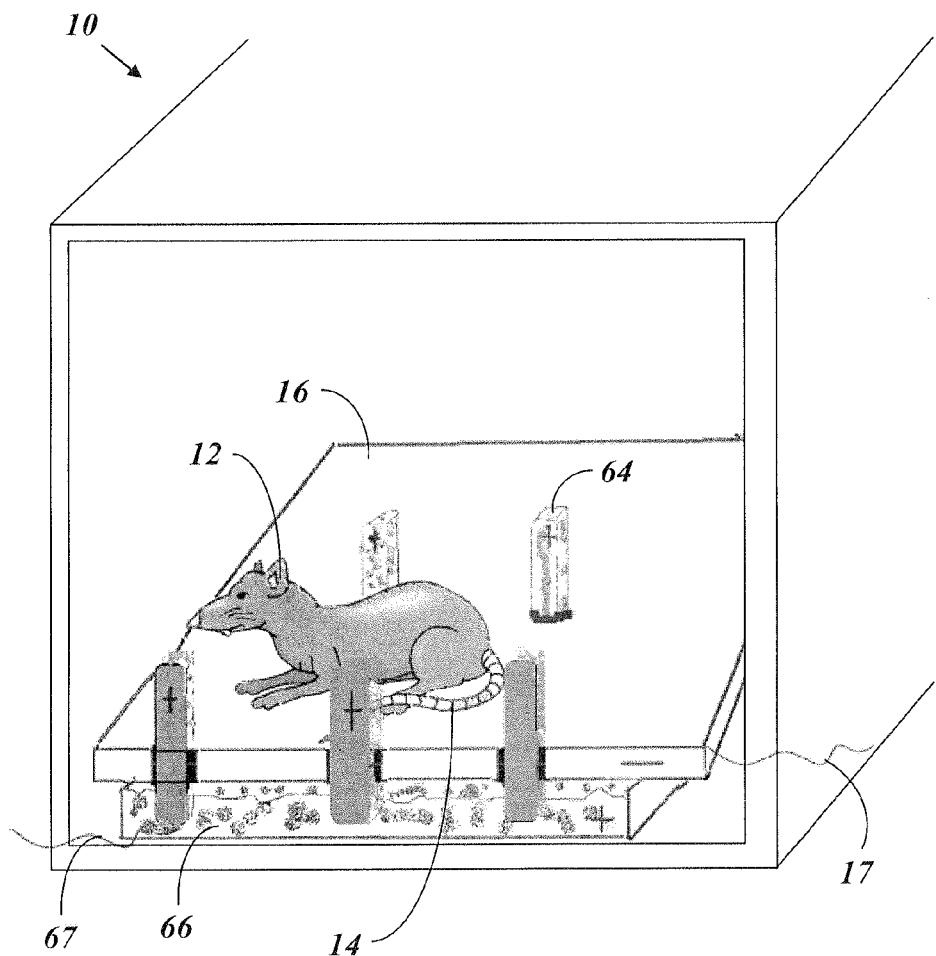
FIGS. 14A and 14B are a perspective view and a top view, respectively, of the chamber of FIG. 1 further including electrically conductive posts, according to example embodiments of the present invention.
Figure 14B:
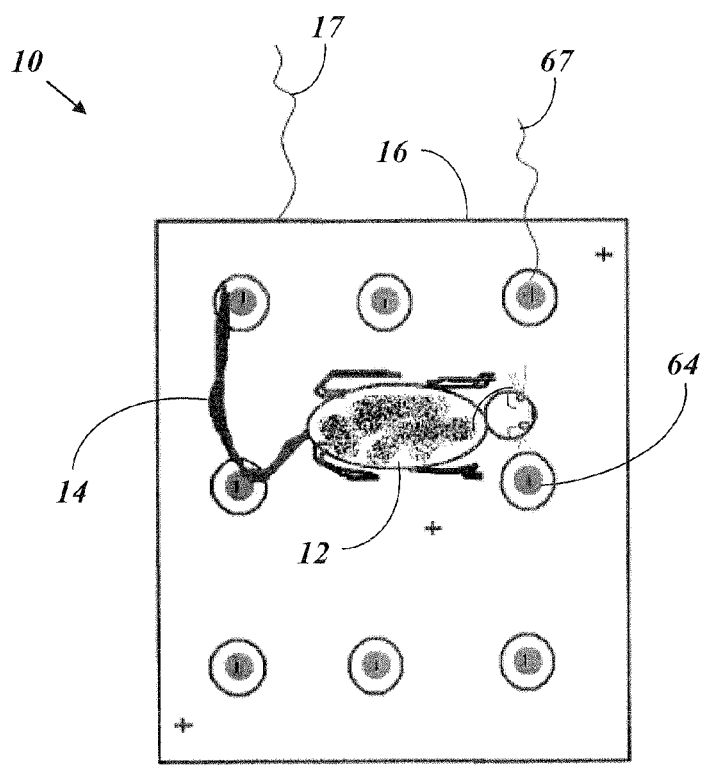

FIGS. 14A and 14B depict another example embodiment of the chamber 10 according to the present invention. In the example embodiment of FIG. 14A and 14B, the entirety of platform 16 constitutes an ECG recording electrode, such that any appendage can contact the floor and establish electrical continuity. Accordingly, the subject 12 is free to explore the entire platform 16 while maintaining an electrical connection. The platform 16 can be made from balsam wood, e.g., with moisture to enhance its electrical conductivity. Other suitable materials can be used, as would be appreciated by one of skill in the art upon reading the present specification.

Continuing with FIGS. 14A and 14B, rising up from the platform 16 are one or more electrically conductive posts 64. Situated below the platform 16 is a reservoir 66 containing an aqueous solution. Lower ends of the posts 64 are situated in the reservoir 66, such that the posts 64 are in electrical contact with the aqueous solution. The posts 64 can be sized and positioned in such a way that the tail 14 of the subject 12 naturally contacts the posts 64, e.g., during exploration of the subject 12 on the platform 16. Accordingly, an electrical connection can be established between the posts 64 and the tail 14 that, in combination with the electrical connection between the subject 12 and the platform 16, allows ECG measurements to be recorded. In one embodiment, the posts 64 are made from balsam wood. Other materials from which the posts 64 can be constructed include one or more of paper, cardboard, parsnip, potato, platinum, stainless steel, or other conductive materials. Thus, the posts 64 contacting the tail 14 of the subject 12 produce an electrical signal that is transmitted to the aqueous solution in the reservoir 66. The reservoir 66 with the aqueous solution contained therein and/or the posts 64 can be coupled (e.g., via a conduit 67) to ECG recording equipment (not shown) to allow electrical signals from any individual post 64 (e.g., and thus the electrical signals from multiple posts 64) to be transmitted to ECG recording equipment.

Additionally, the size and spacing of the posts 64 is such that passage of the subject 12 among the posts 64 is facile and relatively unencumbered. Additionally, the posts 64 can be arranged such that one or more gaps exist to provide the subject 12 with an area suitable for rest. The posts 64 further can be spaced to afford the subject 12 a habitat that is favorable. As just one illustrative and non-limiting example adapted for mice, the primary platform upon which the subject 12 ambulates is about 4 inches by about 4 inches. The posts 64 have a diameter of about ¼ inch, are spaced about 1 inch from each other, and rise up from the platform 16 to a height of about 1 inch. In yet another non-limiting and illustrative example implemented for a rat, the platform 16 is a rectangle shape having dimensions of about 9 inches by about 16 inches. The posts 64 have a diameter of about 0.5 inches and are spaced about 2 inches apart from each other. It should be understood that the shape of the platform 16, as well as the size, spacing, and height of the posts 64 can be configured to accommodate different types of subjects 12. However, the present invention is not limited to the specific examples provided herein. Many alternatives and modifications are possible and contemplated within the scope of the present invention. For example, in some embodiments, the height of the posts 64 can exceed the height of the animal by at least 100%.

If the spacing of the posts 64 is too close, the subject 12 may choose to reside on top of the posts 64, in which case an ECG measurement could not be recorded since the tops of the posts 64 will be electrically all of the same polarity (e.g., positive or negative). Accordingly, the spacing of the posts 64 can be configured such that it is likely that portions of the tail 14 of the subject 12 might be in contact with the posts 64 while portions of the limbs of the subject 12 will be in contact with the platform 16.

Figure 15:
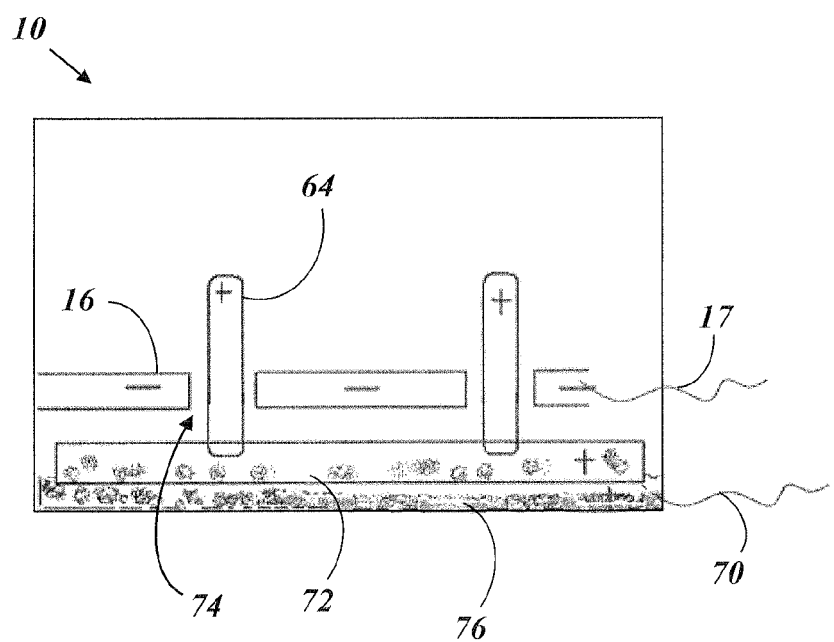
FIG. 15 is a side view of the chamber of FIG. 1 further including electrically conductive posts coupled to a second, lower platform, according to example embodiments of the present invention.

FIG. 15 depicts another embodiment of the chamber 10 in which the posts 64 are maintained in an anchoring element 72 (e.g., a foundation-like structure) situated below the platform 16. Specifically, the posts 64 are maintained in an upright position in the anchoring element 72. The anchoring element 72 is about X inches below the platform 16, to ensure maintenance of electrical polar uniqueness of anchoring element 72 and the platform 16. For example, X can be from about 0 inches to about 2 inches for most rodent subjects. Other distances and values of X may be appropriate depending on the size, type, and agility of the subject 12, as well as the particular dimensions of the second platform 16 and/or the anchoring element 72.

Continuing with FIG. 15, the posts 64 pass up through holes 74 in the platform 16. The holes 74 can have a diameter that is larger than the outer diameter of the posts 64, such that there is a gap between the posts 64 and the platform 16 upon which the subject 12 rests and moves. In the example embodiment depicted in FIG. 15, the anchoring element 72 is in contact with an aqueous solution 76, and the aqueous solution 76 is connected electrically to the ECG recording equipment (e.g., via a conduit 70). Alternatively, the anchoring element 72 can be pre-moistened and/or kept moist to enhance conductivity.

Alternatively to providing a space or gap between the platform 16 and the post 64, the posts 64 alternatively can be held in place by an insulating material situated between the posts 64 and the platform 16, thereby maintaining the outside perimeter of the posts 64 electrically separate from the inside perimeter of the platform 16.

In such example embodiments as those depicted in FIGS. 14A through 15, the platform 50 preferably establishes an electrical connection by contacting the subject 12 at a position forward of (e.g., rostral to) the heart of the subject 12, and the posts 64 preferably establish an electrical connection by contacting the subject 12 at a position rearward (e.g., caudal to) the heart (e.g., the tail 14).

The devices herein described, the instrumented habitat, can likewise apply to the recording of the ECG from other animals with tails, such as monkeys and dogs. One of skill in the art will appreciate a wide variety of other subjects for which embodiments of the present invention can be employed. As such, the present invention is in no way limited to the examples provided herein.

Numerous other modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A chamber device for non-invasively acquiring an electrocardiogram (ECG) of a conscious subject having a tail, the system comprising:
    a chamber;
    a floor of the chamber consisting of a first electrically conductive platform comprising a single conductive plate functioning as a single first electrode for establishing an electrical connection with the subject at a first location of the subject other than the tail, the first electrically conductive platform having a first polarity and being configured to be coupled to ECG recording equipment; and
    a second electrode in the form of an electrical conducting device independent from the first electrically conductive platform for establishing an electrical connection with the tail of the subject, the electrical conducting device having a second polarity opposite from the first polarity and being configured to be coupled to the ECG recording equipment;
    wherein the electrical conducting device is movable relative to the first electrically conductive platform, and further wherein the electrical conducting device is positioned to maintain contact with the tail of the subject in such a way that acquisition of the ECG occurs when the first electrode makes contact with the first location of the subject other than the tail, while the second electrode maintains contact with the tail of the subject.

2. The chamber device of claim 1, wherein the electrical conducting device comprises a moveable electrode.

3. The chamber device of claim 2, wherein the moveable electrode is coupled to a ferrite or magnetic material.

4. The chamber device of claim 2, further comprising an access opening in the chamber device, and further comprising a positioning tool coupled to the moveable electrode and extending through the access opening.

5. The chamber device of claim 1, wherein the electrical conducting device comprises a ringlet configured to fasten around the tail of the subject.

6. The chamber device of claim 1, wherein the electrical conducting device comprises an electrically conductive food element and an electrically conductive conduit situated in the electrically conductive food element.

7. The chamber device of claim 1, wherein the electrical conducting device comprises a second electrically conductive platform that is movable relative to the first electrically conductive platform, wherein the first electrically conductive platform and the second electrically conductive platform are separated by an adjustable amount of space.

8. The chamber device of claim 7, wherein the subject is a neonatal subject and the chamber device forms a channel sized to substantially maintain an orientation of the neonatal subject.

9. The chamber device of claim 7, further comprising a heating element.

* * * * *